United States Patent [19]

Lieb

[11] Patent Number: 4,490,385

[45] Date of Patent: Dec. 25, 1984

[54] TREATMENT OF AUTO-IMMUNE AND INFLAMMATORY DISEASES

[76] Inventor: Julian Lieb, 41 Village La., Bethany, Conn. 06525

[21] Appl. No.: 539,306

[22] Filed: Oct. 5, 1983

Related U.S. Application Data

[62] Division of Ser. No. 319,651, Nov. 9, 1981, Pat. No. 4,409,243.

[51] Int. Cl.³ ............................................. A61K 31/42
[52] U.S. Cl. .................................................... 424/272
[58] Field of Search ......................................... 424/272

Primary Examiner—Stanley J. Friedman
Attorney, Agent, or Firm—Schwartz, Jeffery, Schwaab, Mack, Blumenthal & Koch

[57] ABSTRACT

A method for the treatment of inflammatory disorders and disorders of immunity, which disorders are characterized by excessive prostaglandin E2 biosynthesis, which method comprises administering an effective amount of a monoamine oxidase inhibitor.

1 Claim, No Drawings

TREATMENT OF AUTO-IMMUNE AND INFLAMMATORY DISEASES

This is a division, of application Ser. No. 319,651, filed Nov. 9, 1981, now U.S. Pat. No. 4,409,243.

This invention relates to the treatment of autoimmune and inflammatory diseases such as rheumatoid arthritis, lymphadenopathies, hemolytic anemias, purpura, ankylosing spondylitis, multiple sclerosis, diabetes mellitus, and various disorders of reproduction.

Defects in the biosynthesis and metabolism of prostaglandins are now believed to play an important part in auto-immune and inflammatory disorders. For example, it has been found that the synovial tissues from patients suffering from rheumatoid arthritis produce larger amounts of prostaglandin E2 (PGE2) and prostaglandin F2α (PGF2α) compared to the synovial tissues from unaffected subjects. Similarly it has been found that an increased synthesis of PGE2 and PGF2α occurs in patients exhibiting systemic and gastrointestinal symptoms secondary to food intolerance. Thus, it has been proposed that migraine headaches secondary to the ingestion of certain foods could be the result of an increased synthesis of 2-series prostaglandins.

It has also been proposed that multiple sclerosis is associated with an imbalance in the normal levels of the prostaglandins, PGE1 and PGE2.

There is also evidence to show that many aspects of reproduction may be regulated by the immune system. Thus, it appears that, for example, fertility, pregnancy and labour are at least partially regulated by prostaglandins, which as indicated above are believed to play a part in the immune system. For example, a female's immune system must undergo some change in order that conception may be successful, as her body must accept foreign material i.e. sperm. After conception, her body has to tolerate the fetus, which of course derives half of its genetic material from the father. It is also believed that labour follows a further change in the immune system, and can therefore be regarded as an immune rejection response.

It is understood that prostaglandins play a major role in reproductive physiology. Thus, it is known that excessive prostaglandin synthesis causes dysmenorrhoea and that parturition may be induced by administering prostaglandins intravenously or by insertion of a prostaglandin pessary.

I therefore believe that excessive synthesis of PGE2 also plays a major role in disorders of reproduction, such as infertility, repeated miscarriage, preeclampsia and eclampsia.

Monoamine oxidase (MAO) inhibitors are a class of drugs which have found widespread use in the treatment of depression. Included within this class of compounds are, for example, the substances: phenelzine, iproniazid, isocarboxazid, mebanazine, nialamide, phenoxypropazine, tranylcypromine and pargyline. Iproniazid has also been used as a tuberculostatic agent and in the treatment of angina of effort. Pargyline is primarily used as an antihypertensive agent.

It has been reported that various MAO inhibitors show a potent inhibitory effect on prostaglandin biosynthesis, and primarily on the biosynthesis of PGE2.

I believe that MAO inhibitors are capable of ameliorating the disorders of immunity and inflammatory disorders which are characterised by excessive PGE2 biosynthesis.

Thus, according to the present invention there is provided a method for the treatment of inflammatory disorders and disorders of immunity in a subject, which disorders are characterised by excessive prostaglandin E2 biosynthesis, which method comprises administering to the subject an effective amount therefor of a monoamine oxidase inhibiting drug.

Whilst not wishing to be bound by theory, it is believed that the MAO inhibitors are effective in the method of the invention because of their role in the inhibition of the synthesis of PGE2.

Disorders which may be treated by the method according to the invention are a number of autoimmune and inflammatory diseases in which excessive PGE2 synthesis has been implicated. Such disorders include: (a) rheumatoid and allergic arthritis; (b) certain illnesses induced by viruses, such as Guillain Barre syndrome, infectious mononucleosis, other viral lymphadenopathies and infections with herpes virus; (c) multiple sclerosis and other demyelinating diseases; (d) hematological disorders, such as hemolytic anemias and thrombocytopenias; (e) endocrinologic disorders, such as diabetes mellitus, Addison's disease, idiopathic hypoparathyroidism and chronic lymphocytic thyroiditis; (f) collagen disorders, such as systemic lupus erythematosus; and (g) disorders of reproduction such as amenorrhoea, infertility, recurrent abortions and eclampsia.

Monoamine oxidase inhibitors which may be used in the method according to the invention include all the compounds mentioned above. The precise route of administration and dosage used will of course depend on the particular compound employed in the method of the invention and the type and severity of the condition to be treated. However, the following daily doses for oral administration may be mentioned for guidance: phenelzine. 15 to 90 mg/day; iproniazid, 20 to 120 mg/day; isocarboxazid, 5 to 60 mg/day; mebanazine, 5 to 50 mg/day; nialamide, up to 200 mg/day; phenoxypropazine, 5 to 50 mg/day; pargyline, 5 75 mg/day; and tranylcypromine, up to 60 mg/day.

The following case histories serve to illustrate the method of the invention:

Case No. 1

This 50 year old manic depressive man had a 20 year history of rheumatoid arthritis in his hands and knees. The knee involvement was so severe that he required repeated aspirations. Treatment with a variety of nonsteroidal anti-inflammmatory drugs and butazolidine produced only moderate, temporary relief.

He had taken lithium carbonate, 900 mg./day (serum level 0.5–0.7 mMol/l), for eight years. Lithium controlled episodes of hypomania but did not affect cyclical depression. Tranylcypromine, 20 mg./day, was therefore introduced. After taking the lithium-tranylcypromine combination for three months he reported that he had become completely free of depression and arthritic pain. However, tranylcypromine had also induced insomnia and orthostatic hypotension and discontinuation of tranylcypromine was necessary. Within ten days of stopping tranylcypromine arthritic pain returned. Isocarboxazid, 10 mg. b.i.d., was introduced, and the patient has been entirely free of arthritic pain for more than one year.

Case No. 2

This 42 year old woman suffered from suicidal depressions and food allergies. Chocolate, cheese, spinach, and peanut butter provoked joint pain in her hands and migraine headaches. Citrus fruits precipitated attacks of herpes labialis.

After taking phenelzine, 45 mg./day, for three months she found that she could eat the offending foods without suffering joint pains or headaches. However, she also noticed that her teeth were chipping and noted muscle weakness, ankle instability, and a fine tremor.

As the arthritic pain had remitted it was concluded that phenelzine might have caused excessive inhibition of prostglandin E2 (PGE2) synthesis. In an effort to raise her PGE2 levels an arachidonic acid supplement was introduced in the form of kelp, 2 tablets a day. On three separate occasions she took kelp but on each occasion suffered severe joint pains within an hour, and this approach had to be abandoned.

Case No. 3

This 43 year old woman had taken lithium carbonate for manic depressive illness since the age of 26. At the age of 33 she developed episodes of pain and swelling in her knees and hands and was given a diagnosis of rheumatoid arthritis. She had also suffered from migraine headaches since 18 and from excessive bruising since 20.

At 41 she started taking phenelzine, 15 mg./day for an episode of depression. After taking phenelzine for eight months she reported that there had been no new episode of arthritis, bruising, or headache and she had stopped ibuprofen, which she had been taking intermittently for a number of years.

She remained in remission from depression and arthritis for one year. At this stage she was admitted to a hospital for a hysterectomy. One week before surgery phenelzine was discontinued. Within 48 hours she noticed the return of joint pains. Following surgery she stayed off phenelzine for two weeks and took ibuprofen. She then resumed phenelzine, 15 mg,/day, and was again able to discontinue ibuprofen.

Case No. 4

This 30 year old woman had since puberty suffered from recurrent depressions alternating with hypomanic episodes. She also had frequent episodes of diarrhoea, tinnitus, and abnormal thermoperception. She was able to remove hot plates from an oven with her bare hands without feeling any discomfort and once went swimming in a lake in Canada in the late fall. Between the major mood fluctuations were minor fluctuations which lasted for a few days, and she noticed that her mood was perceptibly better on days when she had diarrhoea.

At age 20 she developed pain and stiffness in her knees and fingers. A diagnosis of rheumatoid arthritis was made and she was placed on indomethacin, but discontinued it because of indigestion.

At age 28 she started to take lithium, 900 mg./day (serum level 0.7–0.85 mEq/l). Her mood stabilized and she experienced a change in temperature perception: She now felt pain on removing hot plates from an oven. At age 29 she had a prolonged episode of depression and was treated with tranylcypromine, 40 mg./day. After two months of tranylcypromine therapy she noticed that her arthritic pain had disappeared, and has had a year's remission from arthritic pain.

Case No. 5

This 53 year old woman had a history of chronic depression characterized by confusion, lack of energy, weakness, and feeling overwhelmed. Migraine headaches began at age 16, and episodes of stiffness and pain in her hips at age 24. She complained of excessive bruising and recurrent labial herpes with an attack frequency of one or two episodes a month.

Phenelzine, 30 mg./day, induced improved mental clarity and increased energy. After taking phenelzine for a month she noted remission of hip pain and stiffness. Remission of depression and arthritis has persisted for ten months on phenelzine therapy, and she has also noticed cessation of bruising and herpes labialis.

Case No. 6

This 40 year old man had a life-long history of phobic anxiety, recurrent depression, and brief hypomanic episodes. At age 32 he started to have episodes of pain and stiffness in his hips. These symptoms were most pronounced on awakening and could be so severe that he could only walk with difficulty.

At age 37 he suffered a career setback and became depressed, with dysphoric affect, early morning awakening, guilt feelings, and an inability to enjoy life. He sought psychopharmacologic consultation and was started on phenelzine, 45 mg./day. The symptoms of depression cleared within ten days. He continued to take the same dose of phenelzine and a month later reported that he was free of his hip symptoms. Remission of depression and arthritis has continued for three years on phenelzine therapy.

Case No. 7

This 24 year old male college student had a ten year history of painful stiff joints and depression. The joint pains began in his knees but later affected his hips and his back so that there were days when he was so severely affected by sciatic nerve pain that he had severe discomfort on walking. The pain was relieved when he sat or lay down. He had allergic rhinitis in response to mold spores, frequent throat infections, and would often become dizzy after drinking sweet drinks or eating peanuts. He had severe reactions to poison ivy, frequent loose stools, gum pain, frequent nose bleeds, and a severe bout of infectious mononucleosis in 1978.

Depression was characterized by feeling blue, helpless, hopeless, and worthless, with loss of interest and crying spells. He looked sad, spoke in a sad voice, and appeared slowed down and lacking in energy. He had insomnia and poor concentration. Blood pressure was 140/100 mmHg.

Ten minutes after taking 5 mg. of tranylcypromine his blood pressure was 120/80. This was not a surprising finding, as the antihypertensive activity of tranylcypromine has been well known. Tranylcypromine dosage was increased over the following few weeks and there followed gradual remission of joint and back pain and depression. At 60 mg. of tranylcypromine per day there was no depression, no pain in the knees or hips, and only minor pain in the sciatic nerve distribution.

Case No. 8

This 36 year old woman sought attention after a four-month history of tremors, depression, noctural vomiting, blurred vision and facial numbness. She stated that it was hard to sight an object and to maintain visual constancy. Objects appeared to vibrate if they moved too quickly. Her right eye seemed heavier than her left and the right side of her face felt larger. She had difficulty distinguishing the laterality of sound. Her face felt heavy and bloated and her skin felt swollen and her right eye sunken in. The optical and facial symptoms would last for a few weeks and then remit.

Other symptoms included anorexia, intention tremor, weakness, headache and a sleep reversal. At times her ataxia was so severe that she had marked instability in walking with a tendency to fall down stairs. The episodes of facial numbness has a history dating back for five years. She also suffered from periodic hair loss.

As a child, this patient was sickly, and had a variety of medical problems including symptoms relating to her kidneys and back, hypotension, dysmenorrhoea, vomiting, headaches, cold intolerance, and tremor. She had a rash on her cheeks, acne, hair loss, and ganglion cysts on her right wrist and her neck. She was subject to upper respiratory tract infections, frequent bouts of painful canker sores, and cervical lymphadenopathy.

On monoamine oxidase inhibitor therapy (tranylcypromine) 30 mg./day she experienced significant improvement in depression and the neurological symptoms. The facial symptoms remitted, as did the vertigo, the vomiting, the tremor, and the ataxia. There was, however, little effect on the sleep reversal.

Case No. 9

This 75 year old woman is the aunt of Case No. 8. Her medical history was characterized by the onset of depression and anorexia following a cold in February, 1981. Gradually symptoms of depression set in, with a feeling of helplessness and worthlessness, loss of interest, crying spells, fatiguability, poor concentration, insomnia, and tearfulness. By the beginning of May, 1981, she developed ataxia, tremor, vomiting, facial anesthesia, and vertigo.

She took tranylcypromine, 10 mg. t.i.d., and within two weeks there was complete remission of depression and neurological symptoms.

Case No. 10

This 54 year old woman had severe attacks of multiple sclerosis in 1967 and 1968 and became incapacitated from the illness in October, 1979, following another major attack. At this point she was unable to move her legs and she became bedridden.

Other symptoms included migraine headaches, hypertension, manic depression, and arthritic pain in her joints.

She has a chronic post nasal drip and frequent sore throats and has been described by various physicians as "allergic to viruses".

She took lithium, 20 mg. b.i.d., which stabilized her hypomanic instability but did nothing for her neurological symptoms or her hypertension. Phenelzine, 60 mg. a day, remitted her headache and joint pains and induced gradual improvement in motor strength and coordination. She has now been able to take a few steps.

Case No. 11

This 34 year old woman sought attention with an acute depressive episode. She also reported symptoms of premature menopause, i.e., amenorrhoea for two years and hot flashes. Within one month of treatment with phenelzine 15 mg./day, she had a period. She continued to menstruate regularly. There is evidence that ovulation was occurring as she would become sexually aroused approximately 14 days before her periods and she noticed a thick clear vaginal secretion at this time.

After nine months therapy with phenelzine she decided to discontinue it because of weight gain. Two months after stopping phenelzine she became amenorrhoeic and the depression returned, along with the hot flashes. She resumed phenelzine therapy six months after discontinuing it and within a month began to have regular periods and the hot flashes ceased.

Case No. 12

This 27 year old woman had a history of anorexia nervosa and depression. She had been amenorrhoeic for three years when first seeking attention. She was treated with tranylcypromine, 10 mg./day, and in the third month of treatment she menstruated. Menses continued on a regular monthly basis over sixteen months of tranylcypromine therapy. At this stage she discontinued tranylcypromine and within two months was again amenorrhoeic.

Case No. 13

This 32 year old white female developed weight loss, depression, and amenorrhoea at age 19. Four months after starting therapy with phenelzine she reported consistently good mood and her first menstrual period in 13 years. On maintenance phenelzine therapy, she resumed a normal menstrual pattern.

Case No. 14

This 31 year old woman had a history of recurrent depression and a two year history of infertility. She had had an extensive workup for infertility but no pathology could be identified.

She took tranylcypromine for her depression and within three months of starting tranylcypromine she conceived. At term she delivered a normal, healthy, full term, male infant.

Case No. 15

This 34 year old woman had a history of depression, depersonalization, impaired concentration, purpura, mucous colitis, and three spontaneous abortions.

On administration of tranylcypromine she reported cessation of depression, bruising, depersonalization, and improved concentration. After taking tranylcypromine for a year she conceived out of wedlock. Because of her previous pregnancy history she expected to abort spontaneously. At 14 weeks this had not occurred and she elected to have the pregnancy terminated. She stated that she felt physiologically similar to her state during the aborted pregnancies, and was convinced that tranylcypromine had prevented a spontaneous abortion.

I claim:

1. A method for the treatment of arthritis in a subject which method comprises administering to the subject a monoamine oxidase inhibiting effective amount of isocarboxazid.

* * * * *